US006897954B2

(12) United States Patent
Bishop et al.

(10) Patent No.: US 6,897,954 B2
(45) Date of Patent: May 24, 2005

(54) INSTRUMENT SETUP SYSTEM FOR A FLUORESCENCE ANALYZER

(75) Inventors: James E. Bishop, Santa Cruz, CA (US); Sunil S. Dalal, Hayward, CA (US); Zhenxiang Gong, Cupertino, CA (US); Michael D. Lock, Mountain View, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 243 days.

(21) Appl. No.: 10/326,524

(22) Filed: Dec. 20, 2002

(65) Prior Publication Data

US 2004/0119974 A1 Jun. 24, 2004

(51) Int. Cl.$^7$ .............................. G01N 21/64; G01J 3/30
(52) U.S. Cl. .................................... 356/317; 250/459.1
(58) Field of Search ................................ 356/317–318, 356/417; 250/458.1–461.2; 436/172

(56) References Cited

U.S. PATENT DOCUMENTS 5,314,824 A * 5/1994 Schwartz ................. 250/461.2

FOREIGN PATENT DOCUMENTS

WO    WO 01/28700 A1    4/2001

OTHER PUBLICATIONS

Bagwell, C.B.; Adams, E.G. "Fluorescence Spectral Overlap Compensation for any Number of Flow Cytometer Parameters", Ann. N.Y. Acad. Sci. 677, 167–184 (1993).

Roederer, M. et al., "Eight Color, 10–Parameter Flow Cytometry to Elucidate Complex Leukocyte Hetrogeneity", Cytometry 29, 328–339 (1997).
Shapiro et al, "A Flow Cytometer Designed for Fluorescence Calibration", Cytometry 3, 280–287 (1998).
"BD FACSDiVa™ Option White Paper" Mar., 2002, (BD Biosciences, San Jose, CA; available at www.bdbiosciences.com).
Web Page: "Coulter Epics XL/XL–MCL Brochure p. 11", © 1996, (Coulter International Corporation; downloaded Dec. 1, 2002 from http://scooter.cyto.purdue.edu/pucl_cd/flow/vol3/7/coulter/xl_mcl11.htm).
FACSComp™ Software User's Guide: Three–Color Applications, Jan. 1966, (BD Biosciences, San Jose, CA).
Bagwell, "Software Compensation Laboratory", Presentation at the 25th Annual Course in Flow Cytometry: Research Methods and Applications, Jun. 8–14, 2002, Bowdoin College, Brunswick, Maine, USA.
Baumgarth, "A Practical Approach to Multicolor Flow Cytometry for Immunophenotyping", Journal of Immunological Methods 243, 77–97 (2000).
RCA Corporation, Photomultiplier Handbook, 44–45 Copyright (1980).

* cited by examiner

*Primary Examiner*—F. L. Evans
*Assistant Examiner*—Kara Geisel
(74) *Attorney, Agent, or Firm*—Douglas A. Petry (57) ABSTRACT

The present invention provides instruments for analyzing a multiplicity of fluorescent dyes using a multiplicity of amplifying photodetectors, methods for using the instruments, methods for setting the instrument parameters, and methods for resetting the instrument parameters following a changed in photodetector amplification. The present invention is particularly applicable in the field of flow cytometry.

49 Claims, 3 Drawing Sheets

INSTRUMENT SETUP SYSTEM FOR A FLUORESCENCE ANALYZER

BACKGROUND OF THE INVENTION

1. Field of the Invention

The present invention relates to instruments for analyzing a multiplicity of fluorescent dyes using a multiplicity of photodetectors. The present invention is particularly applicable to the field of cytometry, more particularly, flow or scanning cytometry.

2. Description of Related Art

Particle analyzers, such as flow and scanning cytometers, are well known in the art. In these systems, fluorescently labeled particles, such as molecules, analyte-bound beads, or individual cells, are individually analyzed by exposing each particle to an excitation light, typically one or more lasers, and measuring the resulting fluorescence from each of dye labels. Each particle may be labeled with a multiplicity of spectrally distinct fluorescent dyes. Typically, detection is carried out using a multiplicity of photodetectors, one for each distinct dye to be detected. Both flow and scanning cytometers are commercially available from, for example, BD Biosciences (San Jose, Calif.).

Other instruments systems are known to be capable of detecting a multiplicity of fluorescent dyes using a multiplicity of photodetectors. For example, nucleic acid amplification reaction products from multiple target sequences can be detected and distinquished using fluorescently labeled probes, wherein each target-specific probe is bound to a spectrally distinct dye. Typically, an instrument for analyzing nucleic acid amplification products measures the total fluorescence from a reaction mixture, and the frequency of each target species is determined from the measured fluorescence from each dye.

In flow cytometers and other instruments that employ a multiplicity of photodetectors to detect a multiplicity of dyes, the collected light is separated into specific ranges of wavelengths, typically by a system of frequency-dependent filters and dichroic mirrors, such that the light detected by a particular photodetector is limited to a predefined range of wavelengths, referred to as a detection channel. The detection channels and dyes are selected such that the peak of the emission spectrum of each dye is within the frequency range of a different detection channel, i.e., each detection channel detects primarily the emission from a single dye. However, because of the breadth of the emission spectra of fluorescent dyes, typically a dye will fluoresce in more than one detection channels and, thus, measurements of dye fluorescence are not independent. The emission of one dye in detection channels intended for the detection of other dyes is referred to by a number of terms, such as spillover, fluorescence spectral overlap, and crosstalk.

Methods of decreasing the effect of spillover or crosstalk on the dye fluorescence measurements are known in the art. Such methods involve adjustment of the signal measured by each photodetector by an amount calculated to compensate for the contribution from dyes other than the primary dye to be detected. Examples in the field of flow cytometry include Bagwell, C. B.; Adams, E. G. "Fluorescence Spectral Overlap Compensation for any Number of Flow Cytometer Parameters", Ann. N.Y. Acad. Sci. 677, 167–184 (1993); Roederer, M. et al., "Eight Color, 10-Parameter Flow Cytometry to Elucidate Complex Leukocyte Hetrogeneity", Cytometry 29, 328–339 (1997); and Bigos et al., 1999, Cytometry 36: 36–45, each incorporated herein by refer ence. WinList™ (Verity Software House, Topsham, Me.) is a stand-alone software package that allows software compensation on the stored data files produced by a flow cytometer. See also the whitepaper describing the BD FACSDiVa™ Option for the BD FACSVantage SE Flow cytometer (BD Biosciences, San Jose, Calif.; available at www.bdbiosciences.com), incorporated herein by reference.

In a typical flow cytometric analysis, labeled particles suspended in a liquid medium are passed through a narrow channel one at a time past an interrogation region. Particles are labeled with one or more fluorescent dyes to facilitate identification. While passing the interrogation region, labeled particles are exposed to excitation light, typically from one or more lasers, and the resulting particle fluorescence is measured. Typically, the amount of excitation light scattered by the particles also is measured. The amount of scattered light and the intensity of emitted fluorescent light from each of the bound labels provide a characterization of the labeled particles. Flow cytometry provides a rapid means of analyzing a large number of particles and, importantly, provides data on each individual particle, rather than only on the particle population as a whole. However, the detection of low level of light emitted by the dye molecules bound to a single particle typically requires amplification of the detected signal. To detect such low levels of emitted light, current flow cytometers use photodetectors such as photomultiplier tubes (PMT) and avalanche photodiodes (APD) that are capable of amplifying the signal. Such photodetectors are capable of amplifying the signal amplifiction by a factor of $10^6$ or greater. The amplification gain of a PMT or APD can be varied by adjusting an input voltage to the detector, or by adjusting the gain of a downstream amplifier, or both.

Instruments for the detection of labeled nucleic acid amplification products typically measure labeled products at the population level, rather than at the level of individual particles, and the degree of signal amplification required depends on the volume of sample analyzed. Signal amplification, if used, can be achieved using an amplifier in-line with the detector output. As with a PMT or APD, the amplification gain typically is adjustable.

Prior to carrying out a particular assay using a flow cytometer, photodetector signal amplification (gain) and the signal range detected are adjusted based on the brightness/amount of dyes to be detected in order that the sample measurements are within the dynamic range of the detection system. To provide maximum resolution of sample fluorescence level, it is desirable that the photodetector gain and the detected signal range are set such that the expected range of sample fluorescence spans a significant portion of the detectable range. As the expected range of sample fluorescence is sample-specific, these instrument parameters must be determined and set prior to analyzing each kind of sample. In addition, these parameters are specific to the instrument, as individual instruments will differ in their performance.

Photodetector gain and the detected signal range typically are set in a flow cytometer by analyzing samples of standards that are representative of the unknown sample to be analyzed subsequently. For example, before analyzing a cell-containing sample, a sample of beads or cells dyed with an amount of dye representative of the expected brightness of a brightly-dyed cell is used to set the upper end of the detection range, or a sample of unlabeled beads or cells that fluoresce at a level of an unlabeled sample cell are used to set the lower end of the detection range. This determination of appropriate settings typically is carried out each day, even if the same type of analysis is to be carried out each day, in part because of day-to-day variation in instrument and photodetector performance.

Because the levels of photodetector gain in each of the multiple photodetectors affects the measurement of light in each channel, the amount of spillover fluorescence measured is dependent on the photodetector gains. Using current flow cytometers, the relative amounts of spillover fluorescence from the dyes, used to determine compensation, are experimentally determined after the photodetector gain settings have been chosen. Any change to the instrument's photodetector gain settings after the initial setup renders the measurements of spillover and, hence, the compensation, no longer applicable to current instrument settings. The relative amounts of spillover fluorescence from the dyes must be redetermined experimentally using the current instrument settings, and the compensation is redetermined from the experimental results.

SUMMARY OF THE INVENTION

The present invention provides instruments for analyzing a multiplicity of fluorescent dyes using a multiplicity of amplifying photodetectors, wherein the instruments comprise stored representations of the pairwise functional relationships between measured fluorescence and signal amplification of the photodetector (photodetector gain) for each of the photodetectors and for each of the fluorescent dyes. The representations can be stored in a firmware or software component of the instrument. The stored representation of the functional relationships enables a number of useful novel features, including the calculation of compensation for any given set of photodetector gain settings, and the recalculation of compensation after changing the photodetector gain settings, without the need to analyze additional samples. The elimination of the need to analyze additional samples after adjusting one or more photodetector gain settings represent a significant improvement over previous instruments. The instrument of invention enables a number of advantageous features that make use of the stored functional relationships.

The functional relationships may be determined each time the set-up procedure is carried out, or may be determined less frequently. It is anticipated that, depending on the stability and consistency of the photodetector and associated signal processing used, it may be sufficient to determine the functional relationship once, such as upon installation of the photodetector into the instrument. The functional relationships preferably are determined empirically, but may be determined in whole or in part from the physical properties of photodetector used.

In another aspect, the present invention provides methods for determining compensation in an instrument for analyzing a multiplicity of fluorescent dyes using a multiplicity of photodetectors, wherein the instrument comprises a stored representation of the pairwise functional relationships between measured fluorescence and photodetector gain for each of the photodectors and for each of the fluorescent dyes; wherein the method comprises:

a) selecting an initial set of photodetector gain settings; and b) calculating compensation for the initial set of photodetector gain settings using the stored relationships.

In a preferred embodiment, the functional relationships are determined as part of the instrument setup. Thus, the present invention provides methods for determining compensation in an instrument for analyzing a multiplicity of fluorescent dyes using a multiplicity of photodetectors, said method comprising:

a) determining and storing a representation of the pairwise functional relationships between measured fluorescence and photodetector gain for each of the photodectors and for each of the fluorescent dyes;

b) selecting an initial set of photodetector gain settings; and c) calculating compensation for the initial set of photodetector gain settings using the stored relationships.

Following the initial selection of photodetector gain settings and the determination of correct compensation for those settings, the instrument settings may be further optimized. For example, an analysis of a sample using the initial instrument settings may result in fluorescence data that is not in a desired region within the data space. An adjustment of at least one photodetector gain setting may be made such that the sample fluorescence would be measured within a more desired region. The adjustment can be made either by direct adjustment of the parameter that controls photodetector gain, or indirectly by manipulating some feature of the data, such as fluorescence level, that is affected by photodetector gain.

The present invention enables indirect adjustment of photodetector gains, wherein a desired fluorescence level for a labeled particle is specified, the photodetector gain that would result in the desired output is calculated using the stored functional relationship, and the photodetector gain is set to the calculated value. In a preferred embodiment, the data are displayed using a graphical representation and the user indicates the desired results by manipulating the graphical representation of the data. For example, the sample data may be displayed in a dot-plot or a histogram on a video screen, e.g., as is commonly used in the analysis of flow cytometric data, and the user may select and alter the displayed data using a computer pointing devices, such as a mouse. Using the stored functional relationships, the system alters photodetector gain settings such that the desired results would be obtained if the sample fluorescence were measured again.

The present invention allows automatic recalculation of the compensation following adjustment of one or more of the photodetector gains, directly or indirectly, without the need to analyze additional samples. Thus, the present invention provides methods for setting compensation of an instrument for analyzing a multiplicity of fluorescent dyes using a multiplicity of photodetectors, wherein the instrument comprises stored representations of the pairwise functional relationships between measured fluorescence and photodetector gain for each of the photodectors and for each of the fluorescent dyes; wherein the method comprises:

a) selecting an initial set of photodetector gain settings;

b) calculating compensation for the initial set of photodetector gain settings using the stored relationships;

c) adjusting at least one photodetector gain to obtain an adjusted set of photodetector gain settings; and d) recalculating compensation for the adjusted photodetector gain settings without analyzing additional samples.

In a preferred embodiment, the functional relationships are determined as part of the instrument setup. Thus, the present invention provides methods for setting compensation of an instrument for analyzing a multiplicity of fluorescent dyes using a multiplicity of photodetectors, said method comprising:

a) determining and storing a representation of the pairwise functional relationships between measured fluorescence and photodetector gain for each of the photodectors and for each of the fluorescent dyes;

b) selecting an initial set of photodetector gain settings;

c) calculating compensation for the initial set of photodetector gain settings using the stored relationships;

d) adjusting at least one photodetector gain to obtain an adjusted set of photodetector gain settings; and e) recalculating compensation for the adjusted photodetector gain settings without analyzing additional samples.

In a preferred embodiment, the instrument is a cytometer, more preferably, a scanning or flow cytometer. However, the present invention is applicable to any instrument for analyzing a multiplicity of fluorescent dyes using a multiplicity of photodetectors, each having an adjustable gain, in which compensation is desired, i.e., wherein spectral overlap of the dye emission spectra results in one or more of the photodetectors measuring light from more than one dye. In a preferred embodiment, photomultiplier tubes (PMT) are used as photodetectors and the functional relationship determined is the relationship between the input voltage of the photodetector and the measured fluorescence, or between the logarithm of input voltage of the photodetector and the logarithm of the measured fluorescence.

In general, depending on the photodetector and associated amplifiers and/or signal processors used, the functional relationship of the underlying variables may be a non-linear relationship. A transformation may be applied to either or both the measured fluorescence and the photodetector gain, and the functional relationship between the transformed variables determined. Such transformation of the variables is particularly desirable in the case that the functional relationship between transformed variables is approximately linear, as linear relationships can be represented in a concise manner in an instrument. For example, in a flow cytometer using PMT photodetectors, the functional relationship between the logarithm of the PMT voltage and the logarithm of the fluorescence is approximately linear over most of the PMT voltage range. Thus, the relationship is well approximated by a linear function of the transformed variables, $$\mathrm{Log}(O) = C_1 \cdot \mathrm{Log}(V) + C_2,$$

wherein O is the observed fluorescence intensity, V is the PMT voltage, and $C_1$ and $C_2$ are constant coefficients determined by fitting the line to empirically determined data. The stored representation of the functional relationship can be simplified by recording only the constants define the linear function, i.e., storing the values $C_1$ and $C_2$ for each dye.

Another aspect of the invention is a simplified method of recalculating compensation following an indirect adjustment of photodetector gains. In this method, the compensation is recalculated by direct modification of the initial compensation matrix using the ratio of the desired fluorescence level to the initial fluorescence level. The simplified method of calculating an adjusted compensation matrix is particularly useful after an indirect adjustment of the photodetector gain settings wherein the user selects a desired fluorescence level for a population of particles that differs from the level measured at the initial photodetector gain settings. The present invention provides a method of calculating an adjusted compensation matrix from an initial compensation matrix following adjustment of a photodetector, comprising the steps of:

a) defining a brightness ratio, r, as the ratio of desired fluorescence level to the fluorescence level measured using the initial photodetector gain settings;

b) multiplying the row of the initial compensation matrix corresponding to the adjusted photodetector by r to obtain a row-adjusted compensation matrix;

c) multiplying the column of the row-adjusted compensation matrix corresponding to the primary dye for the adjusted photodetector by 1/r to obtain the adjusted compensation matrix.

One property of the simplified method of calculating an adjusted compensation matrix is that it enables the adjustment of a compensation matrix that has been modified ("tweaked") by the user by changing one or more of the compensation values without the user having to reenter the matrix modifications after compensations is recalculated. A tweaking of the compensation matrix typically is made if the experimental sample (e.g., cells) have different properties than the standard samples (e.g., labeled beads) used in instrument setup and, thus, a modification of the compensation calculated from the standard samples would provide a more accurate analysis of the experimental sample. Recalculation, after a change in photodetector gain, of compensation based on the stored functional relationships will restore the correct compensation applicable to the standard particles, thus eliminating the user's adjustments. In contrast, the simplified method of calculating an adjusted compensation matrix enables recalculation of the tweaked compensation after a change in photodetector gain, wherein the effect of the tweak is maintained after recalculation.

In embodiments wherein the stored functional relationships are linear relationships between the logarithm of the PMT voltage and the logarithm of the fluorescence, the brightness ratio depends on the slope ($C_2$, in the above equation) of functional relationship. Thus, simplified method of calculating an adjusted compensation matrix can be carried out referring only to the slopes from the stored functional relationships combined with the data (measured fluorescence, photodetector gain setting) obtained from an sample. It will be clear that the combination of previously stored slope information and stored data from a sample comprising measured fluorescence obtained at a known photodetector gain setting provides a complete representation of the functional relationship equivalent to stored representation comprising the slope and intercept, as described above.

Another aspect of the present invention is the recalculation of correct quantitation after a change in photodetector gain. In setting up an instrument to carry out quantitative estimates of dye amount, quantitation standards having a known amount of dye are analyzed to calibrate the system. The present invention enables the recalculation of correct quantitation without the need to analyze additional sample of a quantitation standard.

Another advantage of the present invention is that functional relationships for a large number of dyes can be stored in the system, thus enabling flexible application-dependent selection of specific subsets of dyes. In addition, functional relationships for additional or novel dyes can be added incrementally to the system without the need to re-determine the previously determined functional relationships.

DETAILED DESCRIPTION OF THE INVENTION

Figure 1:
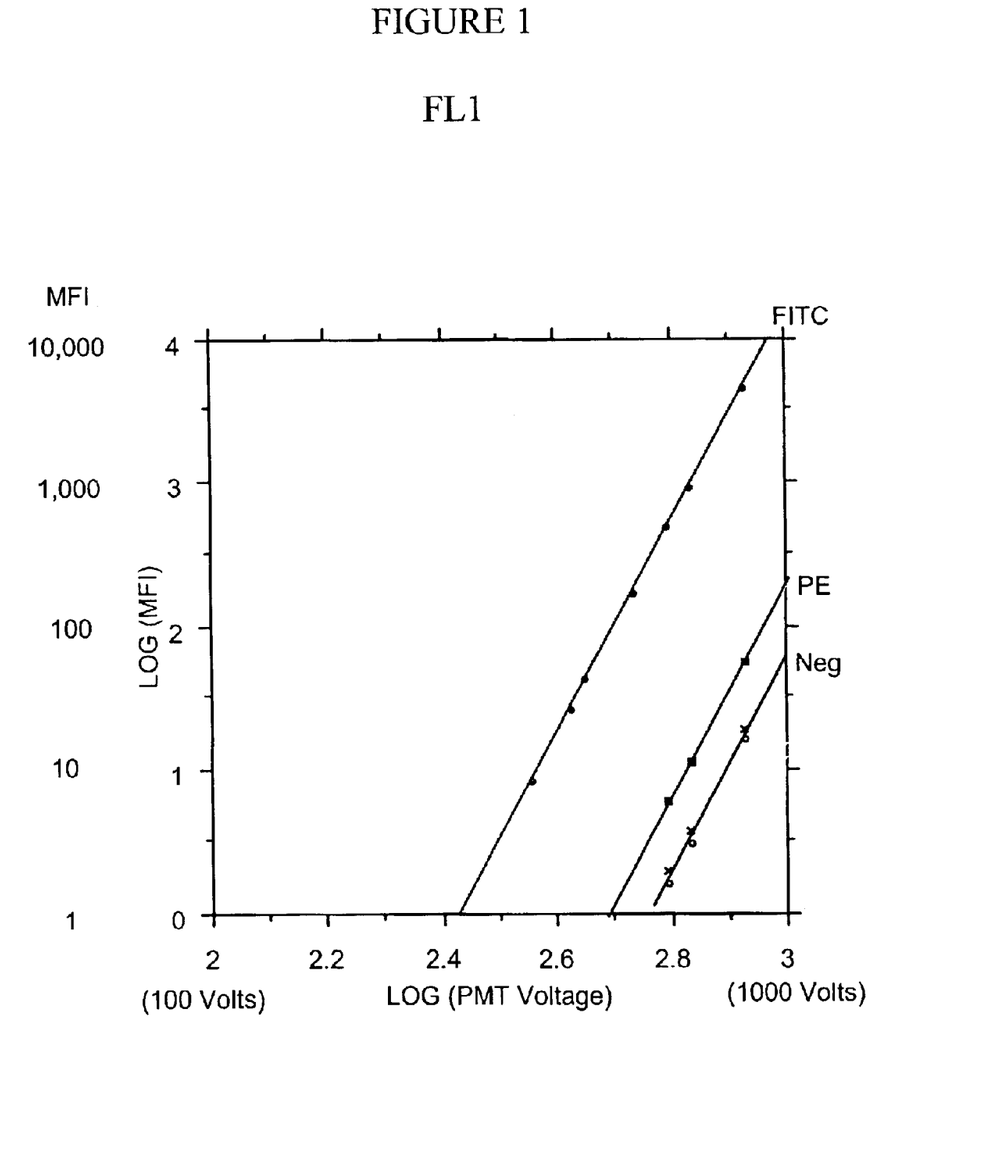
FIG. 1 shows a representative plot of the relationships between the logarithm of the mean fluorescence intensity (MFI) and the logarithm of PMT voltage for FITC-dyed beads, PE-dyed beads, and undyed beads (replicated) in Fluorescence channel 1 (FL1), as described in Example 1.
Figure 2:
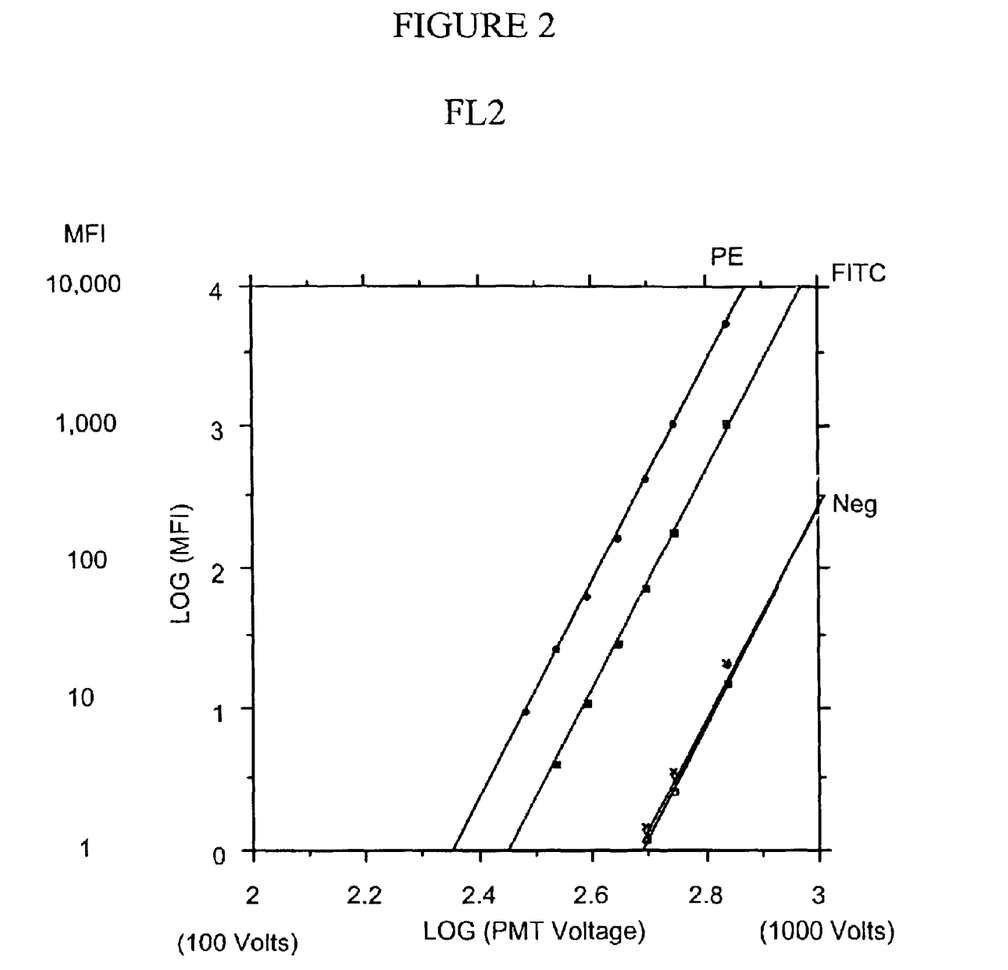
FIG. 2 shows a representative plot of the relationships between the logarithm of the mean fluorescence intensity (MFI) and the logarithm of PMT voltage for FITC-dyed beads, PE-dyed beads, and undyed beads (replicated) in Fluorescence channel 2 (FL2), as described in Example 1.
Figure 3:
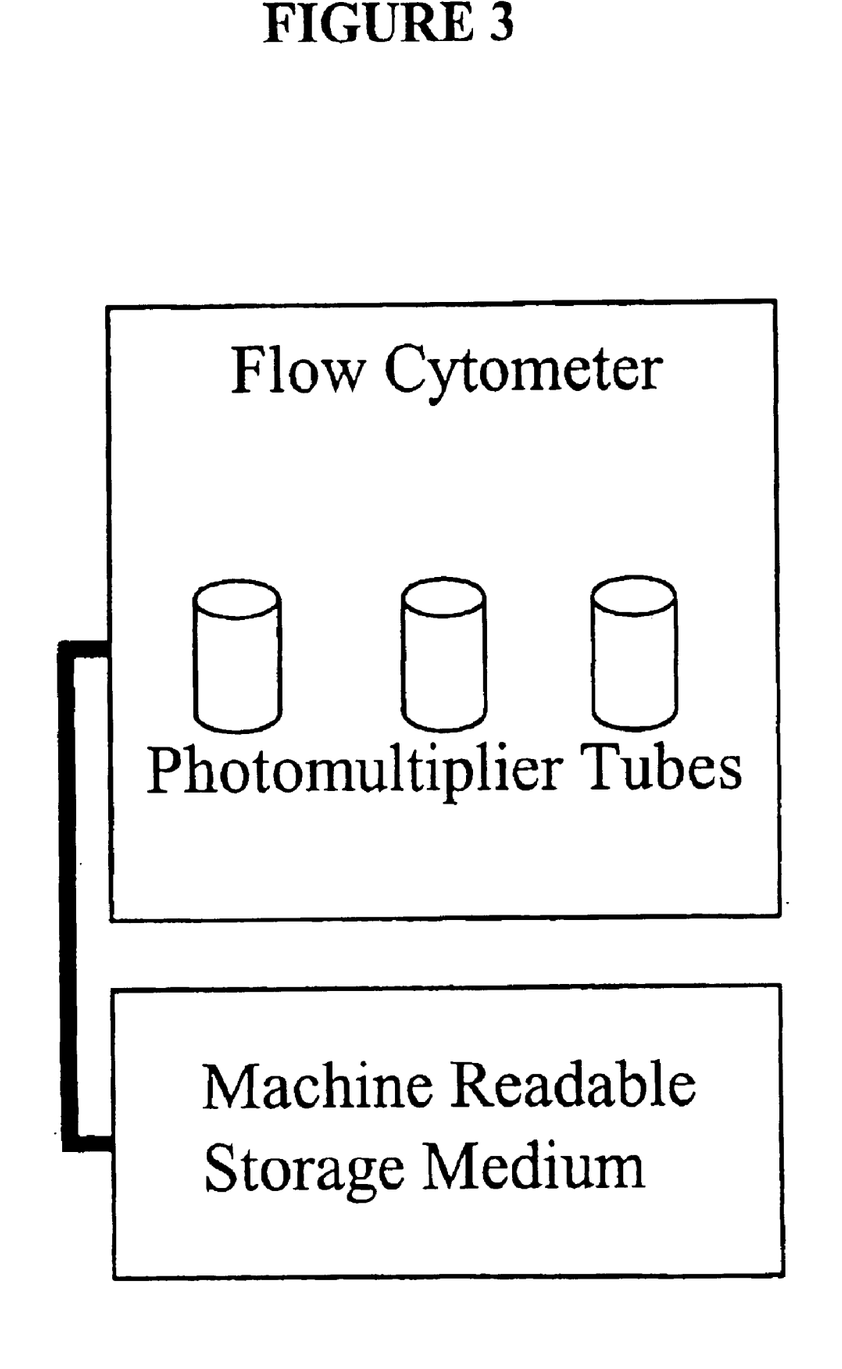
FIG. 3 shows a diagram of an embodiment of the instrument of the present invention.

The following definitions are provided for clarity. Unless otherwise indicated, all terms are used as is common in the art. All reference cited herein, both supra and infra, are incorporated herein by reference.

As used herein, "system" and "instrument" are intended to encompass both the hardware (e.g., mechanical and electronic) and associated software (e.g., computer programs) components.

As used herein, a "representation of a functional relationship" refers to any representation that allows determining the output variable for a given input variable over the range of variables of interest. The term is intended to encompass representations of approximations of a true functional relationship, such as obtained by fitting a line or polynomial to empirical data. Furthermore, the term is intended to encompass representations of a functional relationship between transformed variables.

As used herein, "particle population" refers to a group of particles that possess essentially the same optical properties with respect to the parameters to be measured, such as cells of the same type (cell population), or synthesized beads that, within practical manufacturing tolerances, are of the same size, shape, and composition (bead population). For example, unlabeled 6-micron beads, 6-micron beads labeled with a specific dye at a first concentration, and 6-micron beads labeled with a second specific dye at a second concentration could constitute three distinct bead populations. Beads can consist of particles of any shape and need not be spherical.

The present invention relates to instruments that have multiple photodetectors, each having an adjustable signal amplification, also referred to as gain. It is not critical whether the photodetector gain is provided by a photodetector alone or by a signal amplifier that amplifies the output of the photodetector. For this reason, "photodetector" is used herein to refer to either a photodector alone or a photodetector with accompanying signal amplifier(s), if present. For example, the signal from a photodiode, which has a fixed intrinsic response, or a avalanche photodiode, which has an adjustable amplification, but which typically used at a fixed amplification level, may be passed through either a linear or logarithmic signal amplifier providing an adjustable gain; the photodetector gain in this case refers to the amplification provided by the combination of the photodiode and the signal amplifier. In preferred embodiments, photomultiplier tubes are used, which provide signal amplification. However, additional amplification of the photodectector output may be used. For example, in the BD FACSDiVa™ Option for the BD FACSVantage SE Flow cytometer (both from BD Biosciences, San Jose, Calif.), the signals from the photomultiplier tubes are passed through a pre-amplifier before being converted to a digital signal by an analog-digital converter.

The methods of the present invention are based on a determination of the pairwise functional relationships, for each photodetector, between measured fluorescence and a parameter that is used to set the signal amplification (gain) of the photodetector. For example, the input voltage level of a PMT is the parameter that is used to set the signal amplification of the PMT, and is the parameter that is adjusted during instrument setup. As another example, in the case that photodiodes or avalanche photodiodes are connected to a downstream adjustable amplifier, the parameter that is used to set the signal amplification of the downstream amplifier is the parameter that is adjusted during instrument setup. For convenience, the value of the parameter that is used to set the photodetector gain will be referred to interchangeably as the photodetector gain, as is customary in the art. Thus, for example, the input voltage of a PMT (or, simply, the PMT voltage) will be used as the measure of PMT gain.

A "detector channel" or "detection channel" refers to the range of wavelengths that is detected by a specific photodetector. Typically, a plurality of non-overlapping detector channels are measured to facilitate the independent measurement of a plurality of spectrally distinct fluorescent dyes. The range of wavelengths detected typically is determined by the use of frequency-dependent filters and/or dichroic mirrors, as is well known in the art.

Typically, dyes and detector channels are selected such that, as much as is feasible, the emission maximum of each dye is within a different detector channel, i.e., such that each dye is matched to a detector channel optimized to detect light from that dye. However, due to the breadth of its emission spectrum, light from a given dye may be emitted within one or more other detector channels. The light emitted by a dye within a detector channel other than the detector channel that most closely matches the emission maxima of the dye is referred to herein as "spillover".

The detector channel that most closely matches the emission maximum of a dye is referred to herein, with reference to the given dye, as the dye-detection channel or primary channel. All other detector channels are referred to, with reference to the given dye, as spillover channels or secondary channels. A dye and its dye-detection channel will be referred to as "corresponding" or "matched." With reference to a detection channel, the dye that corresponds to the detection channel is referred to as the primary dye; dyes that emit spillover into the detection channel are referred to as secondary dyes.

Compensation refers to the process of effectively removing from the total amount of light detected within a detector channel the contribution due to spillover from dyes other than the primary dye, i.e., the contribution from the secondary dyes. Thus, after compensation, the amount of light detected from a single detector channel represents a measure of the light emitted by a single dye, specifically, the primary dye. Compensation facilitates analysis of the data from multiply dyed particles by making the measurements of each of the dyes independent.

Compensation

To help in understanding the invention, the general principles of compensation are described for an instrument having n channels for detecting n dyes. It is assumed that the n channels and n dyes are numbered such that the primary detection channel for each dye has the same number as the dye (e.g. channel 2 is used to detect dye 2). So numbered, spillover is the dye fluorescence measured by a detector channel having a different number. This numbering scheme is chosen for convenience and elegance of presentation and is not a critical aspect to the invention.

Let $O_i$ denote the total fluorescence measured (observed) in the ith detector channel, which is the sum of the individual flourescences measured from each dye. Let $D_j$ denote the fluorescence of dye j in detector j, i.e., the fluorescence measured by the matched detector channel. Then the fluorescence of the jth dye in the ith channel can be written as $(S_{ij} \cdot D_j)$, where $S_{ij}$, referred to as a spillover coefficient, is the relative fraction of $D_j$ detected in channel i. By definition, $S_{ii}=1$. The total fluorescence measured in the ith detector channel can be written as $$O_i = \Sigma S_{ij} \cdot D_j, \quad (1)$$

where the summation is over the n dyes detected. Equation (1) provides a system of n equations, one for each detector channel.

Compensation is used to determine the fluorescence of each dye in its matched dye-detector channel (each $D_j$) from the total fluorescence measured in each channel, which includes contributions from dye spillover. Compensation is carried out by simultaneously solving the system of equations for the $D_j$. It should be noted that, in a system without spillover, wherein the emission of each dye is detected only by its dye-detection channel, equation (1) simplifes to $O_i=D_i$ for all i, and no compensation is necessary.

For compactness, the above system of equations, and the mathematics of compensation correction, are described herein using matrix algebra. However, it will be clear that this representation is for convenience and clarity of presentation and that other representations of the system of equations may be used and are equivalent. In particular, it will be clear that a software implementation need only carry out equivalent calculations, but that the details of a software implementation are not a critical aspect of the invention.

1. Basic Compensation

Let O be the n×1 column vector of fluorescence measurements in each of the n channels, i.e., $O=[O_1, \ldots O_n]^T$. O represents the vector of observed, uncompensated measurements. Let D be the n×1 column vector of dye fluorescence for each of the n dyes, i.e., $D=[D_1, \ldots D_n]^T$. D represents the vector of compensated measurements. Let S be the n×n matrix of spillover coefficients, $S_{ij}$. Then, the system of equations represented by equation (1) can be written in matrix form as $$O = S \cdot D \quad (2)$$

and the compensated fluorescence values, D, are obtained by left-multiplying both sides of the above equation with the inverse of the spillover matrix, $$S^{-1} \cdot O = D. \quad (3)$$

The inverse of the spillover matrix is called the compensation matrix.

The spillover matrix can be estimated by measuring the fluorescence of single dye in each detector channel, and repeating this for each dye. The measurements of the same dye (or same population of dyed particles) in each detector channel correspond to one column of the spillover matrix. The fluorescence measurements in each column are normalized by dividing by the fluorescence measured in the primary detection channel to obtain the relative spillover coefficients. Given the ordering of the channels and dyes chosen, the resulting spillover matrix has ones on the diagonal ($S_{ii}=1$) and the off-diagonal coefficients correspond to the relative spillover into the detector channels intended for the measurement of different dyes.

To facilitate discussions of the spillover matrix, because the coefficients within a single column of the spillover matrix correspond to the fluorescence measured from the same population of dyed particles in each of the channel, a single column of the spillover matrix will be referred to as corresponding to a particular dye. Similarly, because the coefficients within a single row of the spillover matrix correspond to the fluorescence measured from the different populations of dyed particles in a single channel, a single row of the spillover matrix will be referred to corresponding to the photodetector. The compensation matrix will be referred to in the same manner. Thus, the same column in the compensation matrix and spillover matrix will be referred to as corresponding to the same particular dye, and the same row in the compensation matrix and spillover matrix will be referred to as corresponding to the same particular photodetector.

2. Compensation with Autofluorescence

In the above description of compensation, it is assumed that the fluorescence of each dye is measured directly. However, in some embodiments, particularly wherein the instrument is a flow cytometer, only particles within a given size range are measurable and dye molecules must be bound to a particle of a suitable size to be measurable. In practice, the fluorescence of a dye is measured in a flow cytometer by labeling a bead or cell population with a uniform amount of dye and measuring the fluorescence of the labeled bead or cell population. However, unlabeled beads or cells may fluoresce in one or more of the detector channels. This fluorescence of unlabeled beads or cells, referred to as autofluorescence, raises the background level of fluorescence detected in each channel. To obtain an accurate estimate of the true fluorescence from each dye, the autofluorescence from the particle to which the dye is bound is subtracted from the measured fluorescence intensities before the spillover matrix is estimated.

Let A be the n×1 column vector of autofluorescence for unlabeled particles (e.g., beads or cells) measured in the n channels, i.e., $A=[A_1, \ldots A_n]^T$, wherein $A_i$ is the fluorescence measured from an unlabeled particle in channel i. The system of equations, analogous to equation (2), can be written in matrix form as $$O = S \cdot D + A \quad (4)$$

and the compensated fluorescence values, D, are obtained by first subtracting the autofluorescence and then left-multiplying both sides of the above equation with the inverse of the spillover matrix, $$S^{-1} \cdot (O-A) = D. \quad (5)$$

As in the previous case without autofluorescence, the spillover matrix can be estimated by measuring in each detection channel the fluorescence of uniformly labeled bead populations, each population labeled with a single dye, and repeating this for each dye, but the contribution from the bead autofluorescence is removed first. The autofluorescence is determined by measuring the fluorescence of an unlabeled particle population in each detector channel. The autofluorescence, A, is subtracted from the observed measurements, O, before the spillover matrix, S, is estimated. The columns of the spillover matrix are normalized as described above.

Although the spillover matrix typically is estimated by sequentially measuring bead populations labeled with one dye, as described above, it is also possible to simultaneously measure the fluorescence from a mixture of the bead populations. In this case, the bead populations must be distinguishable such that the fluorescence from each dye can be measured independently. Bead populations can be distinguished based on the dye labels if the emissions are adequately distinct, or on any other property of the beads that enables distinguishing the bead populations, such as bead size. In flow cytometry, the process of selectively analyzing a subpopulation of particles identified by a subset of the measured properties is referred to as gating.

It should be noted that S and $S^{-1}$ correspond to the spillover matrix and compensation matrix for the dye-only fluorescence, without the contribution of autofluorescence. Before a vector of fluorescence measurements obtained from a sample particle are compensated using $S^{-1}$, the autofluorescence vector is subtracted from vector of fluorescence measurements. After compensation, the autofluorescence vector, A, is added back to the vector of compensated fluorescence measurements, D. Thus, compensation of incoming data is carried out in the following steps:

1. subtract the autofluorescence vector, A, from the vector of observed fluorescence, O;
2. left-multiply (O−A) by the compensation matrix, $S^{-1}$, to obtain the vector of compensated fluorescence, D; and
3. add A to D to obtain a compensated particle with the autofluorescence properties of the original, uncompensated particle.

These three steps can be reduced to two by rearranging equation 5 as follows:

$$D+A=S^{-1}\cdot(O-A)+A=S^{-1}\cdot O-S^{-1}\cdot A+A=S^{-1}\cdot O+(I-S^{-1})\cdot A,$$

where I the n×n identity matrix. Thus, compensation of incoming data is carried out equivalently in the following two steps:

1. left-multiply the vector of observed fluorescence, O, by the compensation matrix, $S^{-1}$ (without first subtracting autofluorescence).
2. add $(I-S^{-1})\cdot A$ to obtain a compensated particle with the autofluorescence properties of the original, uncompensated particle.

Because $(I-S^{-1})\cdot A$ is a constant-valued vector independent of the data collected during sample analysis, it needs to be computed only once, prior to sample analysis, and the stored value used during sample analysis.

In flow cytometry, because of the need for high speed data handling, autofluorescence is often ignored during the acquisition of data from samples. The error introduced by ignoring autofluorescence is that a constant value, different for each channel, is added to each of the fluorescence measurements, but the amount added is the same for all particles. This can be seen by noting that applying compensation to the observed values without subtracting autofluorescence yields $$S^{-1}\cdot O=D+S^{-1}\cdot A. \tag{6}$$

Note that $S^{-1}\cdot A$ is a vector of constant-valued terms derived from the vector of autofluorescence measurements and is the same for each measurement of a dyed particle. Thus, this represents an vector of constant-valued error terms added to each vector of compensated fluorescence values. In practice, autofluorescence typically is small relative to dye fluorescence, and the error may be acceptable to obtain higher data throughput.

As noted above, S and $S^{-1}$ correspond to the spillover matrix and compensation matrix in the absence of autofluorescence, and is applied to the vector of fluorescence measurements obtained from a sample particle after the autofluorescence vector is subtracted. This autofluorescence vector need not be identical to the vector measured from the unlabeled beads used during the determination of compensation and, in practice, will often not be identical. For example, although standard setup beads may be used to set compensation, the experiment may involve the analysis of cells that possess an autofluorescence different from that of an unlabeled bead. If these differ significantly, the autofluorescence vector that is subtracted from the vector of measurements from each cell during acquisition of data from the experimental sample should be the autofluorescence vector specific to the unlabeled experimental sample particles. This autofluorescence vector is measured separately by analyzing unlabeled cells.

Instrument Setup

In the methods of the present invention, instrument set-up will comprise one or more the following steps:

1. determination of the functional relationship between photodetector gain and measured fluorescence for each dye;
2. storage of a representation of the functional relationship between photodetector gains and measured fluorescence for each dye;
3. selection of initial photodetector gain settings;
4. calculation of compensation for the initial photodetector gain settings;
5. test run of sample to determine the range of observed result values;
6. selection of adjusted photodetector gain settings;
7. calculation of compensation correction for the adjusted photodetector gain settings;

An advantage of the present invention is that it enables the adjustment of instrument settings without the need to run additional samples. Each of these steps is described in detail, below.

1. Determination of the Functional Relationship Between Photodetector Gain and Fluorescence for Each Dye The methods of the present invention are based on a determination of the pairwise functional relationships, for each photodetector, between measured fluorescence and a parameter that is used to set the signal amplification (gain) of the photodetector. For example, the input voltage level of a PMT is the parameter that is used to set the signal amplification of the PMT, and is the parameter that is adjusted during instrument setup. For convenience, the value of the parameter that is used to set the photodetector gain will be referred to interchangeably as the photodetector gain, as is customary in the art. Thus, for example, the input voltage of a PMT (or, simply, the PMT voltage) will be used as the measure of PMT gain.

Equivalently, the pairwise functional relationships between measured fluorescence and photodetector gain can be determined following application of a transformation to the variables, such as a logarithm function. Such transformations typically are applied in order to obtain a linear functional relationship. In a preferred embodiment, the functional relationship determined is between the logarithm of the measured fluorescence and the logarithm of the photodetector gain.

The functional relationship is a physical property of the photodetector and light collection optics (filters and/or mirrors) that define the detection channel. Preferably, the functional relationship is determined empirically, but may be determined in whole or in part from the physical properties of the photodetector and light collection optics.

In a preferred method for empirically determining the functional relationship using a flow cytometer, the fluorescence of a sample of dye-labeled beads is measured in a each channel at multiple photodetector settings. The functional relationship in each channel is then determined from the measured data. The desired number of different photodetector settings used to estimate the functional relationship will depend in part on the physical properties of the photodetector.

Preferably, the functional relationship for each dye is determined separately by measuring the fluorescence of a bead population uniformly labeled with that one dye in each channel at multiple gain settings. However, it is also possible to simultaneously measure the fluorescence from a mixture of bead populations, each bead population uniformly labeled with a different dye. In this case, the bead populations must be distinguishable by appropriate gating. Such gating can be based on the dye labels if the emissions are adequately distinct, or on some other property of the beads, such as size.

The functional relationships may be determined each time the set-up procedure is carried out, or may be determined less frequently. It is anticipated that, depending on the stability and consistency of the photodetector and associated signal processing used, it may be sufficient to determine the functional relationship once, such as upon installation of the photodetector into the instrument. Because current photodetectors may not be sufficiently stable to provide consistent results, it is preferable to determine the functional relationships on a more frequent basis.

It should be noted that, for a photodetector within its usable range, the inverse of the functional relationship is well defined and, thus, either the fluorescence intensity corresponding to a given photodetector gain or the photodetector gain corresponding to a given fluorescence intensity can be calculated. The methods of the present invention make use of the ability to calculate either variable as a function of the other variable, as described below.

2. Representation of the Functional Relationship

Preferably, the functional relationship is determined from the empirical data, obtained as described above, by fitting a function to the data, and using the fitted function as an approximation of the true functional relationship. Methods for fitting a function to data are well known in the art. In a preferred embodiment, a line or higher order polynomial (a line being a polynomial of degree 1) is fitted to the data using a least-squares approximations, and the resulting polynomial used as the true relationship.

The functional relationship between measured fluorescence and photodetector gain, or an approximation thereof obtained by fitting a function to empirical data, is stored in any manner that allows calculations of an output value given a specific input value. The representation typically will be stored on a machine-readable medium, such as a computer disk or in memory, accessible by the software controlling the instrument. Data structures for representing functions and algorithms for evaluating functions are well known in the art.

In embodiments wherein the functional relationship is a line or higher order polynomial, or approximately so, the representation can be stored efficiently by storing only the parameters that define the function. Computer data structures useful for efficiently storing and evaluating polynomial functions are known in the art and useful in the present invention. For example, the terms of a polynomial may be represented by a list of constant coefficients, with the variable and exponent of each term being implicitly defined by the ordering of the coefficients. Alternatively, a polynomial may be represented by a list of only the non-zero constant coefficients, each stored pairwise with the exponent, the variable again being stored implicitly.

As discussed above, the functional relationship between measured fluorescence and the photodetector gain can be determined using transformed variables, such as the logarithm of one or both the measured fluorescence and the photodetector gain. In a preferred embodiment, the functional relationship between the logarithm of the measured fluorescence and the logarithm of the photodetector gain is determined, fitted to a line, and the parameters that define the line are stored as the functional relationship. Calculation of an output value using the functional relationship of the transformed variables is carried out by solving the represented equation for the untransformed variable.

For example, in a flow cytometer using PMT's, such as a BD FACSCalibur™ flow cytometer (BD Biosciences, San Jose, Calif.), the functional relationship between the logarithm of the PMT voltage and the logarithm of the fluorescence is approximately linear over most of the PMT voltage range. Thus, the relationship is well approximated by a linear function of the transformed variables, $$\mathrm{Log}(O) = C_1 \cdot \mathrm{Log}(V) + C_2, \tag{7}$$

wherein O is the measured fluorescence intensity, V is the PMT voltage, and $C_1$ and $C_2$ are constant coefficients determined by fitting the line to empirically determined data. The stored representation of the functional relationship can be simplified by recording only the constants that define the linear function, i.e., storing the values $C_1$ and $C_2$ for each dye. It will be clear that a linear relationship can be represented equivalently by storing the slope of the equation ($C_1$) and data representing one point on the line, such as the fluorescence measured from a sample at a given PMT voltage.

Using the above stored linear functional relationship between the logarithm of the PMT voltage and the logarithm of the fluorescence, the fluorescence corresponding to a given voltage, and the voltage corresponding to a given fluorescence, are calculated using the following equations, both derived directly from the stored functional relationship:

$$O = 10\textasciicircum(C_1 \cdot \mathrm{Log}(V) + C_2) \tag{8}$$

$$V = 10\textasciicircum((\mathrm{Log}(O) - C_2)/C_1) \tag{9}$$

The symbol "^" is used herein to indicate an exponent; the notation 10^X is equivalent to the notation $10^X$.

3. Selection of Initial Photodetector Gain Settings

An initial set of photodetector gain settings is chosen, preferably as an approximation of the settings likely to be useful for the assay contemplated. The initial set may be default values stored in the instrument, estimated based on the expected fluorescence of the reagents used in the particular assay, or determined experimentally, possibly in previously carried out experiments. Alternatively, an initial set gain settings based on the properties of the particular setup beads used may be determined and provided by the manufacturer or supplier of the beads.

Suitable set of initial photodetector gain settings can be determined empirically by analyzing a set of standards that are representative of the unknown sample to be analyzed subsequently. The photodetector gain settings are adjusted until the measurements obtained from a sample of known brightness are within the desired range. The selection of a suitable set of initial photodetector gain settings is well known in the art and, for example, is carried out routinely in the setup of current flow cytometers.

For convenience, the set of photodetector gain settings will be denoted herein as a vector, $V = [v_1, \ldots v_n]$, wherein $v_i$ is the gain setting for photodetector i.

4. Calculation of Compensation for the Initial Photodetector Gain Settings

Once an initial set of photodetector gain settings is chosen, the compensation is calculated using on the stored representations of the functional relationship between the measured fluorescence and photodetector gain. In practice, this involves determining the values of a compensation matrix. The compensation matrix is determined either by calculating the values in the spillover matrix and then inverting the spillover matrix to obtain the compensation matrix or, equivalently, by directly calculating the values in the compensation matrix. The compensation matrix is stored in the instrument for subsequent use.

The elements of the spillover matrix are determined using the stored representations of the functional relationships between measured fluorescence and photodetector gain. Because, for each dye, the same labeled bead population was used to determine the functional relationships in each detection channel, the relative fluorescence of the dye measured in each detection channel is obtained for any specific set of photodetector gain values by evaluating each of the functional relationships at the given photodetector gain values.

To describe this formally, let $f_{ij}(v_i)$ represent the fluorescence from dye j measured in channel i as a function of the photodetector gain for detector i. The $f_{ij}(v_i)$ are either the stored functional relationships, or, in the case that the stored relationships were between transformed variables, are derived from the stored relationships by solving for the fluorescence as a function of photodetector gain. Thus, for example, if the stored functional relationships are of the form of equation (7), $Log(O)=C_1 \cdot Log(V)+C_2$, then the $f_{ij}(v_i)$ are of the form of equation (8), $O=10^\wedge(C_1 \cdot Log(V)+C_2)$.

Let F(v) denote an n×n matrix with functional coefficients $f_{ij}(v_i)$. Evaluating the function coefficients at a particular set of photodetector gain settings, V, provides a matrix with constant coefficients for the given set of photodetector gains. The constant coefficients within a single column correspond to the fluorescence of the same population of dyed particles in each of the channels using the specified set of photodetector gain settings.

To calculate compensation in the basic no-autofluorescence case, a spillover matrix is obtained by normalizing each column by dividing each term by the fluorescence measured by the primary detector, which should be the maximum value within that column. Equivalently, a generalized spillover matrix, S(v), whose elements are functions of photodector gain is defined as an n×n matrix with coefficients $$f_{ij}(v_i)/f_{jj}(v_j),$$

again using the dye/detector numbering system described above in which the spillover fluorescence is represented by the off-diagonal elements. Once the photodetector gain settings are selected, the constant-valued spillover matrix specific for the selected settings is obtained by evaluating the function elements of S(v) at the appropriate gain settings. The compensation matrix is the inverse of the spillover matrix, as described above.

For example, using a 3 color detection system without considering autofluorescence, the matrix F(v) of dye fluorescence values is $$\begin{bmatrix} f_{11}(v_1) & f_{12}(v_1) & f_{13}(v_1) \\ f_{21}(v_2) & f_{22}(v_2) & f_{23}(v_2) \\ f_{31}(v_3) & f_{32}(v_3) & f_{33}(v_3) \end{bmatrix}$$

and the corresponding generalized spillover matrix, S(v), is $$\begin{bmatrix} 1 & f_{12}(v_1)/f_{22}(v_2) & f_{13}(v_1)/f_{33}(v_3) \\ f_{21}(v_2)/f_{11}(v_1) & 1 & f_{23}(v_2)/f_{33}(v_3) \\ f_{31}(v_3)/f_{11}(v_1) & f_{32}(v_3)/f_{22}(v_2) & 1 \end{bmatrix}$$

The spillover matrix for any given $V=[v_1, \ldots v_n]$ is obtained by evaluating each of the terms of S(V) at the selected settings, and the compensation matrix is the inverse of the spillover matrix.

To calculate compensation with autofluorescence, let $f_{ia}(v_i)$ represent the fluorescence from an unlabeled particle measured in channel i as a function of the photodetector gain for detector i. Evaluating $f_{ia}(v_i)$ at a particular set of photodetector gains settings, V, provides a vector of autofluorescence values for the given set of photodetector gains. The autofluorescence values are subtracted from each of the coefficients corresponding to fluorescence of a dyed particle to obtain a matrix corresponding to the fluorescence of the dyes alone. The spillover matrix is then obtained by normalizing each column, as described above, and the compensation matrix is the inverse of the spillover matrix.

For example, to calculate compensation using a 3 color detection system with autofluorescence, first autofluorescence is subtracted from the matrix F(v) to obtain the following matrix of dye-only fluorescence:

$$\begin{bmatrix} f_{11}(v_1)-f_{1a}(v_1) & f_{12}(v_1)-f_{1a}(v_1) & f_{13}(v_1)-f_{1a}(v_1) \\ f_{21}(v_2)-f_{2a}(v_2) & f_{22}(v_2)-f_{2a}(v_2) & f_{23}(v_2)-f_{2a}(v_2) \\ f_{31}(v_3)-f_{3a}(v_3) & f_{32}(v_3)-f_{3a}(v_3) & f_{33}(v_3)-f_{3a}(v_3) \end{bmatrix}$$

The corresponding generalized spillover matrix, S(v), is obtained by normalizing the above matrix by dividing each element within a column by the diagonal element. Again, the spillover matrix for any given $V=[v_1, \ldots v_n]$ is obtained by evaluating each of the terms of S(V) at the selected settings, and the compensation matrix is the inverse of the spillover matrix.

5. Test run of sample to determine the range of observed result values;

After the initial compensation is calculated based on the data acquired from setup particles using the initially selected photodetector gain settings, data from a test sample (i.e., an experimental sample) are acquired and the data displayed to insure that the selected photodetector gain settings provide the desired results from the experimental sample. Typically, cytometric data are displayed in one or more histograms or dot plots, as is well known in the art. If, after running a test sample, the data obtained are in the expected or desired region of the data space, the photodetector gain is appropriately set and need not be adjusted.

6. Selection of adjusted photodetector gain settings;

If, after running a test sample, the data obtained are not in the expected or desired region of the data space, one or more photodetector gains can be adjusted. For example, when the data are displayed in a dot plot, it is desirable that the data from negative samples are not compressed against an axis. The photodetector gain can be increased to move the data away from the axis.

The adjustment in the photodetector gain can be made directly or indirectly. Indirect adjustment of the photodetector gain results from the user adjusting a property of the data, which property of the data is affected by the photodetector gains. For example, if it is desired that the mean fluorescent intensity of a sample population be in a particular region of the data space, the use can specify the desired location. The photodetector gains that will result in the mean fluorescent intensity being in the desired location in the data space are then calculated using the stored representations of the functional relationship between the measured fluorescence and photodetector gain. The resulting calculated photodetector gains are recorded as the adjusted photodetector gain settings.-

7. Calculation of compensation for the adjusted photodetector gain settings;

The recalculation of the compensation matrix given the adjusted photodetector gain settings is carried out in the same manner as for the original photodetector gain settings, described above. The appropriate compensation matrix for the adjusted settings is the inverse of the new spillover matrix. The adjusted compensation matrix is stored in the instrument for subsequent use.

Alternatively, recalculation of the compensation matrix is carried out using a simplified procedure wherein the compensation matrix is directly adjusted based on the change in fluorescence resulting from the adjustment in photodetector gain settings. It is anticipated that in practice, optimization will most frequently be achieved through indirect adjustment of the gain, i.e., the user will specify a desired mean fluorescence intensity different from the initially measured mean fluorescence intensity. Alternatively, a new fluorescence level that would result from an adjustment in photodetector gain settings can be calculated from the stored functional relationships. The ratio of the desired or new fluorescence intensity to the initial fluorescence intensity, referred to herein as a brightness ratio, enables a useful simplification in a recalculation of compensation.

Using this simplified method, an adjusted compensation matrix is calculated from an initial compensation matrix based on a desired fluorescence intensity different from an initially measured fluorescence intensity by first defining a brightness ratio, r, as the ratio of desired fluorescence intensity to the initial fluorescence intensity. For clarity, the method is described below by first considering the effect of a change in photodetector gain on the spillover matrix. As an adjustment to a photodetector gain effects the same proportional change to all elements within the row of the spillover matrix corresponding to the adjusted photodetector, the spillover matrix is adjusted by multiplying the row of the spillover matrix corresponding to the adjusted photodetector by r to obtain an adjusted spillover matrix. The adjusted spillover matrix must be renormalized, but this requires renormalization of only one column of the matrix. The only column of the adjusted spillover matrix in which the normalization is affected is the column in which an affected dye measurement was used as the divisor in the normalization of the initial spillover matrix, i.e., the column of the spillover matrix corresponding to the primary dye for the adjusted photodetector. Thus, the adjusted spillover matrix is renormalized by multiplying the column of the adjusted spillover matrix corresponding to the primary dye for the adjusted photodetector by 1/r to obtain a normalized adjusted spillover matrix.

Finally, the adjusted compensation matrix is obtained by inverting the normalized adjusted spillover matrix.

The recalculation after an adjustment of one or more photodetectors of the normalized adjusted spillover matrix in terms of the original spillover matrix can be represented using matrix algebra as follows. Let $S_{old}$ represent the spillover matrix prior to the photodetector adjustments, either calculated using the original photodetector gain settings or, optionally, subsequently modified. Let R be an n×n diagonal matrix with diagonal elements (i,i) equal to the brightness ratio for detector channel i (the brightness ratio of non-adjusted photodetectors are equal to one) and off-diagonal elements equal to zero. The normalized adjusted spillover matrix, $S_{new}$, after adjustment of one or more photodetectors is $$S_{new} = R \cdot S_{old} \cdot R^{-1}$$

The adjusted compensation matrix, which is the inverse of the normalized adjusted spillover matrix, is then $$S_{new}^{-1} = (R \cdot S_{old} \cdot R^{-1})^{-1}$$
$$= R \cdot S_{old}^{-1} \cdot R^{-1}$$

Thus, it is equivalent to apply the same transformation directly to the initial compensation matrix. Applying the transformations directly to the initial compensation matrix, rather than to the spillover matrix, simplifies the method in that it eliminates the need to carry out the matrix inversion step.

It should be noted that, to recalculate an adjusted compensation (or spillover) matrix in view of changes of multiple photodetector gains, adjusted compensation (or spillover) matrices can be calculated sequentially considering each adjusted photodetector one at a time.

Quantitation

In many embodiments, it is desired to obtain a quantitative estimate of the amount (e.g., absolute number of molecules or concentration) of dye present in the sample from the measured fluorescence intensity. Quantitation methods and the mathematics used are well known in the art (see, for example, Pannu et al., 2001, Cytometry 45: 250–258; and Davis et al, 1998, Cytometry 33, 197–205, both incorporated herein by reference). Quantitation involves estimating a measure of the amount of dye as a function of measured fluorescence. Typically, the function is estimated empirically by first measuring a series of quantitation standards having different, known amounts of dye, thus obtaining an estimate of fluorescence as a function of the amount of dye. The amount of dye ("dye" in the equations below) as a function of fluorescence is obtained as the inverse of the function describing fluorescence as a function of the amount of dye. Thus, fluorescence=g(dye), wherein g is a function estimated from the empirical data, and, consequently, dye=$g^{-1}$(fluorescence).

The relationship between the fluorescence and the amount of dye is valid for a specific instrument setup, in particular, for specific photodetector gain settings. As a change in a photodetector gain results in a change in measured fluorescence without any change in the dye particle number, a change in a photodetector gain after the fluorescence/dye ratio is determined requires an adjustment of the ratio to account for the changed measured fluorescence.

One method of obtaining correct quantitative results after a change in photodetector gain settings is to re-estimate g. The fluorescence data obtained from the quantitation standard (used to estimate g) can be adjusted to reflect a change in photodetector gain settings using the stored functional relationships between fluorescence and photodetector gain settings, and the adjusted data used to re-estimate the function g (fluorescence as a function of the amount of dye), and, hence, $g^{-1}$ (the amount of dye as a function of fluorescence), all without the need to run additional quantitation standards at the new gain settings.

An alternative method of obtaining correct quantitative results after a change in photodetector gain settings is to use the originally estimated g, but to adjust new fluorescence data to account for the change in measured fluorescence. To illustrate this, let $fl_{initial}$ and $fl_{new}$ denote the fluorescence from the same amount of dye under the initial and adjusted photodetector gain settings, respectively. The correct amount of dye is obtained from the fluorescence measured after a change in photodetector gain settings by first deriving $fl_{initial}$ from $fl_{new}$ using the stored functional relationships between fluorescence and photodetector gain settings, and then calculating $g^{-1}(fl_{initial})$. In the preferred linear case, $fl_{initial}$ is obtained using the brightness ratio, described above:

$$fl_{initial} = fl_{new} \cdot (fl_{initial}/fl_{new}) = f_{new} \cdot (1/r).$$

Thus, after a change in photodetector gain settings, the amount of dye is obtained as $$dye = g^{-1}(fluorescence \cdot (1/r)).$$

In many application, such as quantitation of the number of dye molecules using flow cytometry, the amount of dye (after subtracting background fluorescence) typically is proportional to measured fluorescence, i.e., the ratio fluorescence/dye is a constant or, equivalently $g(fluorescence) = \alpha \cdot fluorescence$, where $\alpha$ is the proportionality constant. In this case, the above calculation using the brightness ratio, r, simplifies significantly. In this case, $$fluorescence = g(dye) = \alpha \cdot dye, \text{ and}$$

$$dye = g^{-1}(fluorescence) = (1/\alpha) \cdot fluorescence.$$

After a change in photodetector gain settings, $$dye = (1/\alpha) \cdot fl_{new} \cdot (1/r).$$

Thus, the correct amount of dye calculated from the fluorescence measured after a change in photodetector gain ($fl_{new}$), but using the proportionality constant determined at the initial photodetector gain, is obtained by multiplying the calculated amount by 1/r. Equivalently, an adjusted proportionality constant is determined after a change in photodetector gain settings by multiplying the proportionality constant, $\alpha$, determined under the initial photodetector gain settings, by r.

Validation of the Stored Functional Relationship

The accuracy of the stored representations of functional relationship between measured fluorescence and photodetector gain can be assessed by considering a measure of the goodness of fit of the data to the representation. For example, if the true relationship is approximately linear and a least-squares method is used to obtain a best-fit line as the representation of the true relationship, the correlation coefficient, r, provides a measure of the goodness of fit of the data to the line. Alternatively, another measures of the goodness of fit, such as the maximum deviation of the data from the estimated representation, can be used. In any case, the stored representation is judged acceptable (validated) if the measure of goodness of fit exceeds some preset threshold. Otherwise, the results should be flagged as unusable and the source of the problem should be corrected before completing instrument setup. Because any of a number of factors can affect the estimation of the functional relationship, such as the quality of the bead population or the reliability of the instrument itself, unacceptable results may only indicate that some aspect of the instrument or reagents requires attention.

Alternatively, validation can be carried out empirically by using the stored representation to predict an outcome and subsequently measuring the actual outcome. For example, the store representation can be used to obtain an expected mean fluorescence intensity for a bead population using a given photodetector gain, the photodetector gain is then adjusted, a sample of the bead population is analyzed, and the predicted value is compared to actual value obtained.

EXAMPLES

The following examples are put forth so as to provide one of ordinary skill in the art with a complete disclosure and description of how to make and use the present invention, and are not intended to limit the scope of what the inventors regard as their invention. The examples describe a flow cytometry system according to the present invention. However, the particular instruments and systems described in the following examples are exemplary, and should not be considered limiting. It will be clear to one of ordinary skill that the present invention is applicable in general to instruments for analyzing a multiplicity of fluorescent dyes using a multiplicity of photodetectors, each having an adjustable gain, in which compensation is desired, i.e., wherein spectral overlap of the dye emission spectra results in one or more of the photodetectors measuring light from more than one dye.

Example 1

Flow Cytometer Setup

The present example describes setup of a flow cytometry system according to the present invention.

System

A flow cytometer according to the present invention was simulated using a BD FACSCaliburm flow cytometer (BD Biosciences, San Jose, Calif.) with the four-color fluorescence detection option. This cytometer has two lasers, a blue laser (488 nm) and a red diode laser (~635 nm). Photomultiplier tubes (PMT) are used for measurement of dye fluorescence. The wavelength ranges detected for the measurement of forward scatter (FSC) and side scatter (SSC), and in each of the fluorescence detection channels (FL1–FL4), are shown in the table, below.

| Channel | Wavelength Range |
| --- | --- |
| FSC | 488/10 nm |
| SSC | 488/10 nm |
| EL1 | 530/30 nm |
| FL2 | 585/42 nm |
| FL3 | ≧670 nm |
| FL4 | 661/16 |

The detectors are intended to detect fluorescence from the following dyes as the primary dyes.

| Detector | Dye | Dye Abbreviation |
| --- | --- | --- |
| FL1 | fluorescein isothiocyanate | FITC |
| FL2 | phycoerythrin | PE |
| FL3 | peridinin chlorophyll protein | PerCP |
| FL4 | allophycocyanin | APC |

Instrument Setup

It previously was determined experimentally that the functional relationship between the logarithm of the PMT voltage and the logarithm of the fluorescence intensity is approximately linear over most of the PMT voltage range (data not shown). Thus, the relationship is well approximated by a linear function of the transformed variables, $$Log(O) = C_1 \cdot Log(V) + C_2,$$

wherein O is the observed measured fluorescence intensity, V is the PMT voltage, and $C_1$ and $C_2$ are constant coefficients (the slope and intercept, respectively) determined by fitting the line to empirically determined data. The stored representation of the functional relationship is simplified by recording only the constants that define the linear function, i.e., storing the values $C_1$ (slope) and $C_2$ (intercept) for each dye/detector pair.

It should be noted that the slope of the linear relationship between the logarithm of the PMT voltage and the logarithm of the fluorescence does not depend on the dye measured, and the slope estimated from any one dye can be used as the estimate of the slope for all dyes. Thus, the stored representation of the functional relationships need contain only a single copy of the slope ($C_1$) for each PMT.

Determination of the Functional Relationships: Method 1

In one method, the slope and intercept of each linear functional relationship is determined by analyzing samples of beads, each labeled with the single dye. A sample of undyed bead population is analyzed to determine the functional relationship corresponding to autofluorescence. As noted above, the slope estimated from any one dye can be used as the estimate of the slope for all dyes. The slope for each PMT is estimated using the sample of beads labeled with the primary dye for that PMT, as this dye provides the strongest signal.

BD Calibrite™ beads (BD Biosciences, San Jose, Calif.) are used to set the photodetector gains and determine the relative emission of individual dyes in the various detection channels. The BD CaliBRITE beads used include unlabeled beads, beads labeled with FITC, beads labeled with PE, beads labeled with PerCP, and beads labeled with APC. The fluorescence of these beads can be clearly distinguished by appropriate gating, which allows acquiring data from a mixture of all the beads in a single sample tube and separating the data from each bead population by gating. Alternatively, the data can be acquired from each bead population separately. In either case, the fluorescence data acquired from each sample of beads are analyzed separately to estimate the functional relationships.

The PMT voltages are varied during the analysis such that fluorescence data is collected at several different voltage settings. Seven different voltage settings spaced to span the detection range have been used and found to be sufficient to enable an accurate estimate of the functional relationship (data not shown). In other experiments, three different voltage settings have been found to be sufficient (data not shown). More or fewer different voltage settings may be used. Data from 2000 labeled beads were collected at each voltage setting, but more or fewer have been found to be adequate in other experiments (data not shown). In general, a suitable number of data points can be empirically determined for a particular instrument and application, and the validation methods described herein can be used to evaluate the accuracy of the fitted function.

After fluorescence measurements are obtained at multiple voltage settings, the resulting data are log-transformed and then fit to a line using a least-squares method, well known in the art. For each dye-detector pairing, the slope and intercept of the best-fit line are stored in the software that controls the instrument as a representation of the linear functional relationship between the log-transformed variables.

The fluorescence of a single bead population measured by each of the PMT's correspond to a single column of the spillover matrix. As a bead population can be measured by all the detectors simultaneously, the detector PMT voltages of all the detectors can be varied in parallel, and, after each stepwise adjustment of the PMT voltage levels of all the detectors, data collected simultaneously in each channel. Thus, data used to estimate the functional relationships corresponding to one column of the spillover matrix are obtained in a stepwise fashion by measuring in all channels beads from the sample of beads at a different sets of voltage levels.

Data used to estimate the functional relationships corresponding to the other columns of the spillover matrix are acquired either simultaneously (all beads in one tube) or by repeating the procedure using separate samples of beads labeled with the other dyes. Data also are acquired using a sample of undyed beads, either simultaneously or separately, to estimate the functional relationship corresponding to the vector of autofluoresence that is subtracted from the dye fluorescence values before calculating the normalized spillover matrix and compensation matrix.

Determination of the Functional Relationship: Method 2

In an alternative, but equivalent method, the slopes for all detector channels are estimated simultaneously by analyzing a single population of beads that fluoresce in each of the detector channels, such as Rainbow Beads (Spherotech, Inc.; Libertyville, Ill.). A sample of Rainbow Beads is analyzed by measuring the fluorescence in each detector channel simultaneously while the detector PMT voltages for each channel are varied in parallel. The resulting data from each detector are log-transformed, fit to lines by a least-squares method, and the slopes of the best-fit lines are used as the slopes for the detector channels. The intercepts obtained from each of the best-fit lines are specific to the Rainbow Beads and, thus, are not used.

Having determined the slopes for all the linear relationships in the log-transformed variables, the intercepts are measured for each population of singly dyed beads and for undyed beads. Only a single measurement (i.e., at a single set of PMT voltages) of each bead population in each detector channel needs to be taken to determine the intercept, as the slope is already known. However, it may be desirable to take measurements at multiple PMT voltage settings to provide a more accurate estimate of the slope. The measurements of each sample of beads can be made simultaneously in each of the detector channels. Data from the CaliBRITE beads described above can be acquired either simultaneously from a mixture of the beads, or from individual samples of beads. Thus, the intercepts for each functional element within the generalized spillover matrix can be from the analysis of data acquired from a single sample comprising a mixture of the beads.

The fluorescence from the rainbow beads and the CaliBRITE beads can be distinguished by gating on the size of the beads, as measured by forward scatter. Thus, as an additional simplification, data from a mixture of the rainbow beads and all of the CaliBRITE beads can be acquired simultaneously, and the data from each bead population distinguished and analyzed separately by appropriate gating.

The following table provides slopes and intercepts obtained by a method equivalent to the above methods. The table entries are stored in software as a representation of each of the functional relationships. Each of the slopes and intercepts was estimated from data acquired at 7 different voltage settings. In the table, Neg refers to undyed beads used to estimate autofluorescence.

Slopes and Intercepts Calculated for Each detector

| Detector | Slope ($C_1$) | Intercept ($C_2$) | | | | |
|---|---|---|---|---|---|---|
| | | FITC | PE | PerCP | APC | Neg |
| FL1 | 7.34 | −17.8 | −19.7 | −20.3 | −20.3 | −20.2 |
| FL2 | 7.70 | −18.8 | −18.1 | −20.5 | −20.7 | −20.5 |
| FL3 | 7.50 | −19.6 | −18.9 | −17.7 | −19.6 | −20.4 |
| FL4 | 7.50 | −21.1 | −21.2 | −19.3 | −18.3 | −21.1 |

Selection of Intitial PMT Voltage Settings

The stored functional relationships are now used to calculate the PMT voltages values that will result in labeled particles, on the average, being measured in its matched detector channel at a desired fluorescence. For this example, the desired "target" fluorescence values for the setup beads, were obtained from a previous analysis of the same bead populations on a BD FACSCalibur flow cytometer, setup using BD FACSComp setup software (BD Biosciences, San Jose, Calif.) to obtain a "standard" setup. Desired fluorescence values were selected for each of the dyed bead populations to be the fluorescence values obtained under the standard setup. It should be noted that desired fluorescence values are specific to the amount of dye (i.e., inherent brightness) contained by the bead used and, thus, will differ depending on the particular manufacturing lot of beads used.

The PMT voltage settings that would result in the mean fluorescence intensity (MFI) of each bead population to be measured at the target value were obtained using equations of the following form:

Desired $V=10^{\wedge}((\text{Log}(\text{Target } MFI)-C_2)/C_1)$, wherein the constants, $C_1$ and $C_2$, are the stored values specific for each detector channel/primary dye pairing. As discussed above, this equation results from solving the linear equation representing the relationship between the log-transformed observed fluorescence and the log-transformed PMT voltage for voltage as a function of fluorescence. The target fluorescence values and calculated PMT voltage settings are shown in the table, below.

PMT Voltages Calculated to Yield Target Values

| Detector | Target Fluorescence | Calculated PMT Voltage |
|---|---|---|
| FL1 | 1333 | 709.24 |
| FL2 | 1640 | 586.36 |
| FL3 | 2763 | 658.95 |
| FL4 | 1794 | 747.90 |

Computation of Compensation

After selection of PMT voltages, the voltages are used to calculate the measured mean fluorescence intensity for each bead population, both labeled and unlabeled, in each detector channel. The equation used results from solving, for a given dye/detector pairing, the linear equation representing the relationship between the log-transformed fluorescence and the log-transformed PMT voltage for fluorescence as a function of voltage. Thus, the mean fluorescence intensity of a population of particles dyed with the jth dye measured in detector channel i at voltage $V_i$ is $MFI_{ij}=10^{\wedge}(C_{1ij}\cdot\text{Log}(V_i)+C_{2ij})$, wherein $C_{1ij}$ and $C_{2ij}$ are the slope and intercept, respectively, of the stored representation of functional relationship between the log-transformed fluorescence and the log-transformed PMT voltage for the ith detector and the jth dye, and the $V_i$ are the initial voltage settings. As described above, the slope is a property of the PMT, and for each i, the $C_{1ij}$ are the same for all j. The mean fluorescence of the undyed particle population is obtained similarly using the corresponding stored representation.

The results obtained are displayed in tabular form, below. The voltages were selected so that the fluorescence of each primary dye in its corresponding detector channel is the target value.

Fluorescence of Dyed Beads in Each Detector

| Detector | FITC | PE | PerCP | APC | Neg |
|---|---|---|---|---|---|
| FL1 | 1333.0 | 16.8 | 4.2 | 4.2 | 5.6 |
| FL2 | 372.2 | 1640.0 | 6.5 | 4.1 | 6.5 |
| FL3 | 34.8 | 174.3 | 2763.1 | 34.8 | 5.5 |
| FL4 | 2.8 | 2.3 | 179.4 | 1794.0 | 2.8 |

Next, the contribution of autofluorescence is subtracted from the fluorescence of the dyed beads to obtain the fluorescence values for the dyes alone, i.e., without the contribution from the bead itself.

Fluorescence of Dyes (Autofluoresence Removed)

| Detector | FITC | PE | PerCP | APC |
|---|---|---|---|---|
| FL1 | 1327.7 | 11.5 | −1.1 | −1.1 |
| FL2 | 320.7 | 1633.5 | 0.0 | −2.4 |
| FL3 | 29.3 | 168.8 | 2757.6 | 29.3 |
| FL4 | 0.0 | −0.5 | 176.6 | 1791.2 |

In this example, the mean fluorescence intensities measured from PerCP- and APC-dyed beads in FL1 and FL2 were dimmer than from the corresponding undyed beads. It is unlikely that this reflects an actual physical process, such as a quenching of autofluorescence by the dye. More likely, this reflects variability in the measurement of autofluorescence, as there is essentially no spillover of these dyes in these channels. For this reason, negative values obtained following subtraction of autofluorescence are set to zero, thus obtaining the table of adjusted dye fluorescence, shown below.

It may be desirable to set to zero all spillover values whose absolute value is below some threshold. The threshold can be set based on the inherent statistical error, empirically determined, in the fluorescence measurements such that only statistically significant spillover fluorescence is considered. Alternatively, the threshold can be set so that any spillover considered to be insignificant to interpretation of the experimental results is ignored.

Adjusted Fluorescence of Dyes (Autofluorescence Removed)

| Detector | FITC | PE | PerCP | APC |
|---|---|---|---|---|
| FL1 | 1327.7 | 11.5 | 0.0 | 0.0 |
| FL2 | 320.7 | 1633.5 | 0.0 | 0.0 |
| FL3 | 29.3 | 168.8 | 2757.6 | 29.3 |
| FL4 | 0.0 | 0.0 | 176.6 | 1791.2 |

Each column is now normalized by dividing by the fluorescence of the dye in its matched detector channel.

| Normalized Fluorescence of Dyes | | | | |
|---|---|---|---|---|
| Detector | FITC | PE | PerCP | APC |
| FL1 | 1 | 0.0070 | 0.0 | 0.0 |
| FL2 | 0.2415 | 1 | 0.0 | 0.0 |
| FL3 | 0.0221 | 0.1033 | 1 | 0.0164 |
| FL4 | 0.0 | 0.0 | 0.0640 | 1 |

The normalized fluorescence values of the dyes (autofluorescence removed) are the values of the spillover matrix. Thus, for this example, the spillover matrix is $$\begin{bmatrix} 1 & 0.0070 & 0.0 & 0.0 \\ 0.2415 & 1 & 0.0 & 0.0 \\ 0.0221 & 0.1033 & 1 & 0.0164 \\ 0.0 & 0.0 & 0.0640 & 1 \end{bmatrix}$$

and the compensation matrix, which is the inverse of the spillover matrix, is $$\begin{bmatrix} 1.0017 & -0.0070 & 0.0000 & 0.0000 \\ -0.2419 & 1.0017 & 0.0000 & 0.0000 \\ 0.0029 & -0.1034 & 1.0011 & -0.0164 \\ 0.0002 & 0.0066 & -0.0641 & 1.0011 \end{bmatrix}$$

In some situations, it may be desirable to simplify the compensation matrix to allow for faster calculations. Near-zero and near-one terms may be rounded off to zero and one, respectively. Alternatively, the compensation matrix can be normalized by dividing each row by the diagonal element, which results in all diagonal elements being equal to one. Although these approximations simplify the calculations required for compensation, the correctness of the compensation is compromised. The tradeoffs should be considered in deciding if such approximations are appropriate for a particular application.

The compensation matrix is used to adjust the data obtained from each detected particle during the acquisition of data from particles analyzed in an experiment. For each event, i.e., detection of a labeled particle, the set of values measured includes forward scatter (FSC), side scatter (SSC), and the fluorescence intensity in each of the four detector channels. For correct compensation, the vector of autofluorescence values in the four detector channels, FL1, FL2, FL3, FL4, obtained from the previous analysis of unlabeled particles of same type being analyzed in the experiment, is subtracted from the vector of fluorescence measurements obtained from the analyzed particle, and the resulting vector of dye-only fluorescence measurements is pre-multiplied by the compensation matrix to obtain a vector of compensated fluorescence values. The autofluorescence is then added back.

In order to increase the speed of data handling, compensation can be applied to the vector of fluorescence measurements without first subracting the contribution from autofluorescence. As discussed above, the result of not subtracting the autofluorescence is that a vector of constant-valued error terms, different for each channel, is added to the vector of fluorescence measurements, but the amount added is the same for all particles. In the present example, autofluorescence is small relative to dye fluorescence (<½% in all channels), and the deviation from true compensation does not significantly affect the interpretation of the data.

It will be recognized that, as the effect of autofluorescence in this example is small, the spillover matrix and, hence, the compensation matrix, could have been estimated without first subtracting the contribution of autofluorescence. However, modeling studies have indicated that applying a compensation matrix, estimated without first subtracting the contribution of autofluorescence, to data from experimental samples after autofluorescence has been subtracted may result in larger errors than applying a properly estimated compensation matrix to data from experimental samples without first subtracting compensation.

Example 2

Setup Adjustments and Optimization

The previous example describes the setup of a flow cytometer of the present invention. During instrument setup, voltages are set to provide fluorescence intensity measurements within a desired range, and the compensation matrix is derived to provide correct compensation. However, the user may modify the instrument setup further by either direct or indirect adjustment of the PMT voltages, or by adjustment of either the spillover matrix or compensation matrix. As described in this example, the present invention enables adjustments to the instrument setup to be made without the need for additional samples to be run.

Indirect Adjustment of PMT Voltages

A preferred feature enabled by the present invention is the ability to automatically readjust the instrument setup such that the data from the analysis of a population are displayed within a desired region of the dataspace. In a preferred embodiment, this feature is implemented such that the user can select both the population of interest and the desired location within the dataspace by using a computer pointing device, such as a mouse. Most preferably, the feature is implemented such that the a first mouse click indicates the population of interest, and a subsequent mouse click specifies the desired location. The method comprises the following steps:

1. The fluorescence intensity data are graphically displayed, typically a computer display, in a dot plot or a histogram;
2. The user selects a population in the graphical display;
3. The user indicates a target location within the graphical display that is the desired location of the selected population;
4. PMT voltage(s) that will result in the selected population being displayed in the target location are calculated;
5. The PMT voltages are adjusted to the calculated values; and
6. An adjusted compensation matrix is calculated based on the adjusted PMT voltages.

The graphical display of fluorescence intensity data on a computer display in either a dot plot or a histogram is well known and in general use in the field of flow cytometry. The implementation of the display and user interface, including the selection and implementation of appropriate display algorithms, are design choices made for ease of use and commercial suitability, and are not critical features of the invention. Similarly, methods for identifying data clusters that correspond to a population of labeled particles displaying particular characteristics is well known in the art. A preferred algorithm for automatically identifying clusters and defining a region encompassing the population is described in U.S. Patent Application Publication US 2002/

0029235 A1. Use of this algorithm allows the user to select an entire population by indicating a point within the cluster, such as by pointing and clicking with a computer mouse.

After the user has selected the population, the mean fluorescence intensity (MFI) is determined, typically automatically by the cluster finding software. The user then indicates the desired MFI, and the PMT voltage that will result in the MFI of the selected population being measured at a desired value is calculated using the ratio of the desired MFI to the originally measured MFI, referred to herein as a brightness ratio. It will be understood that the repositioning can be based equivalently on the mean, median, maximum, minimum, or other such measure of the population fluorescence, and that the procedure is analogous. The application of the brightness ratio (of MFI) to new calculate new PMT voltages in the system of Example 1 is described below.

Let r be a brightness ratio defined as the ratio, in a particular detection channel, of the desired mean fluorescence intensity at an adjusted PMT voltage to the mean fluorescence intensity measured at the original PMT voltage. Referring to the equations relating MFI to V, $$r = MFI_{new}/MFI_{original} = (V_{new}/V_{original})^{C_1},$$

where $C_1$ is the slope of the stored equation for the particular detector. The PMT voltage required such that a population originally measured with a mean fluorescence intensity $MFI_{original}$ is now measured with a mean fluorescence intensity $MFI_{new}$ is obtained from the above equation by solving for $V_{new}$ as a function of $V_{old}$ and the desired brightness ratio, r, to obtain $$V_{new} = r^{(1/C_1)} \cdot V_{original}.$$

After the adjusted PMT voltage settings are calculated, the voltage settings of the instrument are adjusted to the newly calculated settings.

Compensation Recalculation

Each time a PMT voltage is adjusted, either by the indirect adjustment described above or by any other method, the compensation matrix recalculated either directly or by recalculating the spillover matrix and then inverting the recalculated spillover matrix. The new spillover matrix can be calculated using the adjusted set of PMT voltages in the same manner as the original spillover matrix was calculated based on the original set of PMT voltages. Alternatively, a new compensation matrix (or a new spillover matrix) can be recalculated as an adjustment of the current matrix using the brightness ratio.

As described above, the recalculation of the compensation matrix in terms of the current compensation matrix can be represented using matrix algebra as follows. Let $S_{old}^{-1}$ represent the original compensation matrix calculated using the original set of PMT voltages, optionally subsequently modified (tweaked) by the user. Let R be an n×n diagonal matrix with diagonal elements (i,i) equal to the brightness ratio for detector channel i (brightness ratios for non-adjusted PMT's are equal to one) and off-diagonal elements equal to zero. The new compensation matrix, $S_{new}^{-1}$, after adjustment of one or more PMT voltages is $$S_{new}^{-1} = R \cdot S_{old}^{-1} \cdot R^{-1}$$

Following recalculation, the adjusted compensation matrix is stored in the instrument for subsequent use.

Example 3

Quantitation

Using the system of Example 1, a quantitative measure of the amount of dye on a particle will be proportional to the measured fluorescence of the dye after removing the contribution from autofluorescence. Typically, the relationship between the amount of dye and the fluorescence is estimated empirically by first measuring a series of quantitation standards having different, known amounts of dye, thus obtaining an estimate of fluorescence as a function of the amount of dye. In this case, the fluorescence is proportional to the amount of dye, i.e., $$\text{fluorescence} = \alpha \cdot \text{dye},$$

where $\alpha$ is the proportionality constant. The amount of dye as a function of fluorescence is obtained as the inverse of the function describing fluorescence as a function of the amount of dye. Thus, $$\text{dye} = (1/\alpha) \cdot \text{flourescence}.$$

The relationship between the amount of dye and the fluorescence measured using an initial PMT voltage is adjusted following a change in PMT voltage using the brightness ratio. The brightness ratio, r, is determined from the change in PMT voltage using the stored functional relationships, in the case of direct adjustment, or based on the user's selection, in the case of indirect adjustment. After a change in photodetector gain settings, the correct relationship is $$\text{dye} = (1/\alpha) \cdot \text{flourescence} \cdot (1/r) = (1/(\alpha \cdot r)) \cdot \text{flourescence}.$$

Thus, the correct amount of dye calculated from the fluorescence measured after a change in photodetector gain is obtained after multiplying the proportionality constant, $\alpha$, determined under the initial photodetector gain settings, by r.

We claim:

1. An instrument for analyzing a multiplicity of fluorescent dyes, wherein said instrument comprises
    a multiplicity of photodetectors, each having an adjustable gain; and
    a stored representation of pairwise functional relationships between measured fluorescence and photodetector gain for each of said photodetectors and for each of said fluorescent dyes.

2. The instrument of claim 1, wherein said stored representation is stored in a machine-readable medium.

3. The instrument of claim 1, wherein said instrument is a cytometer.

4. The instrument of claim 1, wherein said instrument is a flow cytometer.

5. The instrument of claim 1, wherein at least one of said pairwise functional relationships is between transformed variables.

6. The instrument of claim 1, wherein said multiplicity of photodetectors comprises a photomultiplier tube, and said gain corresponds to an input voltage.

7. The instrument of claim 6, wherein at least one of said pairwise functional relationships is between transformed variables.

8. The instrument of claim 7, wherein said pairwise functional relationships are functional relationships between the logarithm of the fluorescence and the logarithm of said photodetector input voltage.

9. The instrument of claim 7, wherein said functional relationships are approximately linear functions of the logarithm of the fluorescence and the logarithm of the photodetector input voltage, and said representations of said functional relationships are linear functions, $Log(O) = C_1 \cdot Log$ (V)+$C_2$, wherein O is the observed fluorescence intensity, V is the photodetector input voltage, and $C_1$ and $C_2$ are constant coefficients specific to each functional relationship.

10. The instrument of claim 9, wherein said stored relationships for each pairwise functional relationship comprise the constants $C_1$ and $C_2$.

11. A method for determining compensation in an instrument for analyzing a multiplicity of fluorescent dyes using a multiplicity of photodetectors, each having an adjustable gain, wherein the instrument comprises a stored representation of the pairwise functional relationships between measured fluorescence and photodetector gain for each of the photodectors and for each of the fluorescent dyes; wherein the method comprises:
   a) selecting an initial set of photodetector gain settings; and
   b) calculating compensation for said initial set of photodetector gain settings using said functional relationships.

12. The method of claim 11, wherein said stored representation is stored in a machine-readable medium.

13. The method of claim 11, wherein said instrument is a cytometer.

14. The method of claim 11, wherein said instrument is a flow cytometer.

15. The method of claim 11, wherein at least one of said pairwise functional relationships is between transformed variables.

16. The method of claim 11, wherein said multiplicity of photodetectors comprises a photomultiplier tube, and said gain corresponds to an input voltage.

17. The method of claim 16, wherein at least one of said pairwise functional relationships is between transformed variables.

18. The method of claim 17, wherein said pairwise functional relationships are functional relationships between the logarithm of the fluorescence and the logarithm of said photodetector input voltage.

19. The method of claim 17, wherein said functional relationships are approximately linear functions of the logarithm of the fluorescence and the logarithm of the photodetector input voltage, and said representations of said functional relationships are linear functions, $Log(O)=C_1 \cdot Log(V)+C_2$, wherein O is the observed fluorescence intensity, V is the photodetector input voltage, and $C_1$ and $C_2$ are constant coefficients specific to each functional relationship.

20. The method of claim 19, wherein said stored relationships for each pairwise functional relationship comprise the constants $C_1$ and $C_2$.

21. A method for determining compensation of an instrument for analyzing a multiplicity of fluorescent dyes using a multiplicity of photodetectors, each having an adjustable gain, wherein the instrument comprises a stored representation of the pairwise functional relationships between measured fluorescence and photodetector gain for each of the photodectors and for each of the fluorescent dyes; wherein the method comprises:
   a) determining compensation according to the method of claim 11;
   b) adjusting at least one photodetector gain to obtain an adjusted set of photodetector gain settings; and
   c) recalculating compensation for said adjusted photodetector gain settings without analyzing additional samples.

22. The method of claim 21, wherein said adjusting at least one photodetector gain is carried out directly.

23. The method of claim 21, wherein said adjusting of at least one photodetector gain is carried out indirectly.

24. The method of claim 23, wherein said indirect adjustment is carried out by
   a) analyzing a population of labeled particles to obtain fluorescence data for said population;
   b) displaying said fluorescence data on a graphical display;
   c) selecting said population in said graphical display;
   d) determining a location of said population in said graphical display;
   e) selecting a second location in said graphical display; and
   f) adjusting at least one photodetector gain, using said functional relationships, such that said population is displayed at said second location.

25. The method of claim 24, wherein said graphical display is a dot-plot or a histogram displayed on a video screen.

26. A method for determining compensation in an instrument for analyzing a multiplicity of fluorescent dyes, wherein said instrument comprises a multiplicity of photodetectors, each having an adjustable gain, said method comprising:
   a) determining and storing a representation of pairwise functional relationships between measured fluorescence and photodetector gain for each of said photodectors and for each of the fluorescent dyes;
   b) selecting an initial set of photodetector signal amplification settings; and
   c) calculating compensation for the initial set of photodetector signal amplification settings using said functional relationships.

27. The method of claim 26, wherein said stored representation is stored in a machine-readable medium.

28. The method of claim 26, wherein said instrument is a cytometer.

29. The method of claim 26, wherein said instrument is a flow cytometer.

30. The method of claim 26, wherein at least one of said pairwise functional relationships is between transformed variables.

31. The method of claim 26, wherein said multiplicity of photodetectors comprises a photomultiplier tube, and said gain corresponds to an input voltage.

32. The method of claim 31, wherein at least one of said pairwise functional relationships is between transformed variables.

33. The method of claim 32, wherein at said pairwise functional relationships are functional relationships between the logarithm of the fluorescence and the logarithm of said photodetector input voltage.

34. The method of claim 32, wherein said functional relationships are approximately linear functions of the logarithm of the fluorescence and the logarithm of the photodetector input voltage, and said representations of said functional relationships are linear functions, $Log(O)=C_1 \cdot Log(V)+C_2$, wherein O is the observed fluorescence intensity, V is the photodetector input voltage, and $C_1$ and $C_2$ are constant coefficients specific to each functional relationship.

35. The method of claim 34, wherein said stored relationships for each pairwise functional relationship comprise the constants $C_1$ and $C_2$.

36. A method for determining compensation in an instrument for analyzing a multiplicity of fluorescent dyes, wherein said instrument comprises a multiplicity of photodetectors, each having an adjustable gain, said method comprising:

a) determining compensation according to the method of claim 26;
b) adjusting at least one photodetector gain to obtain an adjusted set of photodetector gain settings; and
c) recalculating compensation for the adjusted photodetector gain settings using the stored representations.

37. The method of claim 36, wherein said adjusting at least one photodetector gain is carried out directly.

38. The method of claim 36, wherein said adjusting of at least one photodetector gain is carried out indirectly.

39. The method of claim 38, wherein said indirect adjustment is carried out by
  a) analyzing a population of labeled particles to obtain fluorescence data for said population;
  b) displaying said fluorescence data on a graphical display;
  c) selecting said population in said graphical display;
  d) determining a location of said population in said graphical display;
  e) selecting a second location in said graphical display; and
  f) adjusting at least one photodetector gain, using said functional relationships, such that said population is displayed at said second location.

40. The method of claim 39, wherein said graphical display is a dot-plot or a histogram displayed on a video screen.

41. The method of claim 39, wherein said location of said population is the mean or median of said fluorescence data for said population.

42. A method, in an instrument for analyzing a multiplicity of fluorescent dyes using a multiplicity of photodetectors, each having an adjustable gain, wherein for each of said photodetectors, one of said fluorescent dyes is a primary dye, and wherein said instrument comprises an initial compensation matrix, of determining an adjusted compensation matrix from said initial compensation matrix following an adjustment of a photodetector gain, wherein said adjustment of a photodetector gain results in a change in fluorescence measured from a dye-containing sample from a first fluorescence level to a second fluorescence level, said method comprising the steps of:
  a) defining a brightness ratio, r, as the ratio of said second fluorescence level to said first fluorescence level;
  b) multiplying a row of said initial compensation matrix corresponding to said adjusted photodetector by r to obtain a row-adjusted compensation matrix;
  c) multiplying a column of said row-adjusted compensation matrix corresponding to the primary dye for the adjusted photodetector by 1/r to obtain an adjusted compensation matrix.

43. The method of claim 42, wherein said initial compensation matrix, prior to said adjustment of a photodetector gain, is tweaked without an accompanying adjustment of a photodetector gain, wherein said tweaking comprises:
  a) adjusting at least one entry of the inverse of said initial compensation matrix to obtain a tweaked spillover matrix; and
  b) inverting said normalized tweaked spillover matrix to obtain a tweaked compensation matrix.

44. The method of claim 42, wherein said instrument is a flow cytometer.

45. A method, in an instrument for analyzing a multiplicity of fluorescent dyes using a multiplicity of photodetectors, each having an adjustable gain, wherein for each of said photodetectors, one of said fluorescent dyes is a primary dye, and wherein said instrument comprises an initial compensation matrix, of determining an adjusted compensation matrix from said initial compensation matrix following an adjustment of a photodetector gain, wherein said adjustment of a photodetector gain results in a change in fluorescence measured from a dye-containing sample from a first fluorescence level to a second fluorescence level, said method comprising the steps of:
  a) defining a brightness ratio, r, as the ratio of said second fluorescence level to said first fluorescence level;
  b) multiplying a row of the inverse of said initial compensation matrix corresponding to said adjusted photodetector by r to obtain an adjusted spillover matrix;
  c) multiplying a column of said adjusted spillover matrix corresponding to the primary dye for the adjusted photodetector by 1/r to obtain a normalized adjusted spillover matrix;
  d) inverting said normalized adjusted spillover matrix to obtain an adjusted compensation matrix.

46. The method of claim 45, wherein said initial compensation matrix, prior to said adjustment of a photodetector gain, is tweaked without an accompanying adjustment of a photodetector gain, wherein said tweaking comprises:
  a) adjusting at least one entry of the inverse of said initial compensation matrix to obtain a tweaked spillover matrix and
  b) inverting said normalized tweaked spillover matrix to obtain a tweaked compensation matrix.

47. The method of claim 45, wherein said instrument is a flow cytometer.

48. A method, in an instrument for analyzing a multiplicity of fluorescent dyes using a multiplicity of photodetectors, each having an adjustable gain, of determining an adjusted quantitative result from an initial quantitative result following an adjustment of a photodetector gain from an initial photodetector gain to an adjusted photodetector gain, wherein said adjustment of a photodetector gain results in a change in fluorescence measured from a dye-containing sample from a first fluorescence level to a second fluorescence level, wherein said instrument comprises a stored functional relationship between quantitative result and fluorescence level, and said quantitative result is proportional to said fluorescence level, determined using said initial photodetector gain, said method comprising the steps of:
  a) defining a brightness ratio, r, as the ratio of said second fluorescence level to said first fluorescence level;
  b) measuring a fluorescence of a sample using said adjusted photodetector gain;
  c) determining an initial quantitative result said fluorescence of said sample using said functional relationship;
  d) multiplying said initial quantitative result by 1/r to obtain said adjusted quantitative result.

49. The method of claim 48, wherein said instrument is a flow cytometer.

* * * * *